United States Patent [19]

Wade

[11] Patent Number: 4,528,288

[45] Date of Patent: Jul. 9, 1985

[54] SUBSTITUTED TRIAZOLO[1,5-C]PYRIMIDINES

[75] Inventor: James J. Wade, Oakdale, Minn.

[73] Assignee: Riker Laboratories, Inc., St. Paul, Minn.

[21] Appl. No.: 490,969

[22] Filed: May 2, 1983

[51] Int. Cl.$^3$ .................. A61K 31/505; C07D 487/04
[52] U.S. Cl. ..................................... 514/258; 544/263
[58] Field of Search ........................ 544/263; 424/251

[56] References Cited

U.S. PATENT DOCUMENTS

| | | | |
|---|---|---|---|
| 3,045,015 | 7/1962 | Miller et al. | 544/263 X |
| 3,046,276 | 7/1962 | Miller et al. | 424/251 X |
| 3,053,844 | 9/1962 | Miller et al. | 424/251 X |
| 3,689,488 | 9/1972 | Dukes | 424/251 X |
| 4,269,980 | 5/1981 | Hardy et al. | 544/256 |

FOREIGN PATENT DOCUMENTS

| | | |
|---|---|---|
| 303036 | 11/1972 | Australia . |
| 1074589 | 2/1960 | Fed. Rep. of Germany . |
| 3029871 | 2/1981 | Fed. Rep. of Germany . |
| 1205144 | 1/1960 | France .............................. 544/263 |
| 859287 | 1/1961 | United Kingdom . |
| 873223 | 7/1961 | United Kingdom . |
| 897870 | 5/1962 | United Kingdom . |
| 898409 | 6/1962 | United Kingdom . |

OTHER PUBLICATIONS

Brown, et al., Chemical Abstracts, vol. 93, 150200z (1980).
Yamazaki, Chemical Abstracts, vol. 95, 150574r (1981).
G. W. Miller et al., J. Chem. Soc., 1963, 5642.
G. W. Miller et al., J. Chem. Soc., 1963, 3357.
W. Broadbent et al., J. Chem. Soc., 1963, 3369.
Temple et al., J. Org. Chem., 1963, 33, 530.
D. J. Brown et al., Aus. J. Chem., 1978, 31, 2505.
D. J. Brown, et al., Aust. J. Chem., 1979, 32, 1585.
D. J. Brown, et al., Aust. J. Chem., 1980, 33, 1147.
Translation of Societa Farmaceuticia Italia Pat. No. 1,205,144, Brown, et al., Aust. J. Chem., 1979, 32, 2713–2726.
La Noce and Giuliani reference described in J. Heterocycl. Chem., 1975, 12, 551–555.

*Primary Examiner*—Diana G. Rivers
*Attorney, Agent, or Firm*—Donald M. Sell; James A. Smith; Robert W. Sprague

[57] ABSTRACT

Substituted triazolo[1,5-c]pyrimidines which are bronchodilators. The pharmacological use of these compounds and pharmaceutical compositions containing these compounds are also described.

8 Claims, No Drawings

SUBSTITUTED TRIAZOLO[1,5-C]PYRIMIDINES

TECHNICAL FIELD

The present invention relates to compounds which are known as triazolo[1,5-c]pyrimidines, and more specifically as 1,2,4-triazolo[1,5-c]pyrimidines. The pharmacological use of these compounds as bronchodilators, and pharmaceutical compositions containing these compounds are also within the scope of the invention.

BACKGROUND OF THE INVENTION

Some 1,2,4-triazolo[1,5-c]pyrimidines are known to the art. Certain 1,2,4-triazolo[1,5-c]pyrimidines are disclosed as being bronchodilators in the patents discussed below, the compounds being referred to therein as triazolo[2,3-c]pyrimidines:

United Kingdom Pat. No. 859,287 discloses 2-amino-1,2,4-triazolo[1,5-c]pyrimidines which are substituted on the pyrimidine ring at the 5, 7 and 8 positions by certain combinations of hydrogen, alkyl, halogen-substituted alkyl, hydroxy-substituted alkyl, alkoxy-substituted alkyl, alkenyl, cycloalkyl, amino, alkylamino, dialkylamino, phenyl, alkylthio, alkoxy and halogen substituents. United Kingdom Pat. No. 898,409 discloses processes for preparing certain of these compounds by subjecting the corresponding 1,2,4-triazolo[4,3-c]pyrimidines to an acid treatment, to an alkaline treatment, or to a heat treatment.

United Kingdom Pat. No. 873,223 discloses 2-amino-1,2,4-triazolo[1,5-c]pyrimidines which are substituted on the pyrimidine ring at the 5, 7 and 8 positions by certain combinations of substituents selected from hydrogen, alkyl, halogen-substituted alkyl, alkoxy-substituted alkyl, alkenyl, cycloalkyl, alkylthio and halogen.

United Kingdom Pat. No. 897,870 discloses 2-alkylamino-1,2,4-triazolo[1,5-c]pyrimidines, 2-dialkylamino-1,2,4-triazolo[1,5-c]pyrimidines, and 1,2,4-triazolo[1,5-c]pyrimidines containing a piperidino or morpholino substituent bonded at the 2-position through the nitrogen atom, which compounds are substituted on the pyrimidine ring at the 5, 7 and 8 positions by certain combinations of hydrogen, alkyl, halogen-substituted alkyl, hydroxy-substituted alkyl, alkenyl and halogen substituents.

The following related articles disclose the synthesis of certain 1,2,4-triazolo[1,5-c]pyrimidines as potential bronchodilators.

G. W. Miller et al., *J. Chem. Soc.*, 1963, 5642, discloses 2-amino- or 2-acetamido-1,2,4-triazolo[1,5-c]pyrimidines (referred to therein as triazolo[2,3-c]pyrimidines) which are substituted on the pyrimidine ring by, for example, hydrogen and alkyl substituents. Certain of these compounds are said to be bronchodilators.

G. W. Miller et al., *J. Chem. Soc.*, 1963, 3357, discloses 1,2,4-triazolo[1,5-c]pyrimidines (referred to therein as triazolo[2,3-c]pyrimidines) which are substituted at the 2-position by hydroxy, halogen, alkoxy, amino or substituted amino substituents and on the pyrimidine ring by alkyl substituents, or alkyl and halogen-substituted alkyl substituents.

W. Broadbent et al., *J. Chem. Soc.*, 1963, 3369, discloses 1,2,4-triazolo[1,5-c]pyrimidines (referred to therein as triazolo[2,3-c]pyrimidines) which are substituted at the 2-position by a mercapto, alkylthio, alkylsulphonyl, or dialkylamino substituent, and on the pyrimidine ring by alkyl substituents or alkyl and halogen-substituted alkyl substituents.

Still other 1,2,4-triazolo[1,5-c]pyrimidines are disclosed in the following articles and patent:

Temple et al., *J. Org. Chem.*, 1963, 33, 530, discloses the compound 8-amino-7-chloro-s-triazolo[1,5-c]pyrimidine-2(3H)-one.

D. J. Brown et al., *Aust. J. Chem.*, 1978, 31, 2505, discloses 1,2,4-triazolo[1,5-c]pyrimidines which are substituted at the 2-position by hydrogen or an alkyl substituent, and on the pyrimidine ring by hydrogen and/or alkyl substituents.

D. J. Brown et al., *Aust. J. Chem.*, 1979, 32, 1585, discloses 1,2,4-triazolo[1,5-c]pyrimidines which are substituted at the 2-position by hydrogen or an alkyl substituent, and on the pyrimidine ring at the 5-position by a halogen, hydrazino, alkyl or alkylthio substituent, and at the 7-position by an alkyl substituent.

D. J. Brown et al., *Aust. J. Chem.*, 1980, 33, 1147, discloses 1,2,4-triazolo[1,5-c]pyrimidines which are substituted at the 2-position by hydrogen or an alkyl or phenyl substituent, and on the pyrimidine ring at the 5-position by a halogen substituent, and at the 7-position by hydrogen or an alkyl substituent.

U.S. Pat. No. 4,269,980 discloses 5-, 7- and 8-(optionally substituted phenyl)-1,2,4-triazolo[1,5-c]pyrimidines. These compounds may be substituted at the 2-position by hydrogen or an alkyl substituent and are anxiolytic agents.

DETAILED DESCRIPTION OF THE INVENTION

The present invention relates to 1,2,4-triazolo[1,5-c]pyrimidines which are bronchodilators. The invention also relates to a method for inducing bronchodilation in a mammal using a 1,2,4-triazolo[1,5-c]pyrimidine of the invention, and to pharmaceutical compositions comprising an effective amount of a 1,2,4-triazolo[1,5-c]pyrimidine of the invention and a pharmaceutically acceptable carrier.

More specifically, the present invention relates to compounds of the formula I

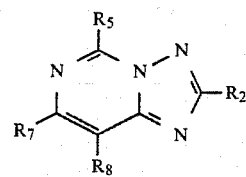

wherein $R_2$ is hydrogen, lower alkyl, mercapto, lower alkylthio, lower alkoxy or hydroxy; $R_5$ is (lower alkyl)amino, di(lower alkyl)amino, alkylthio or benzylthio; $R_7$ is hydrogen, lower alkyl, halogen or lower alkylthio; and $R_8$ is hydrogen, lower alkyl or halogen, and is hydrogen or lower alkyl when $R_7$ is halogen; with the provisos that at least one of $R_5$ and $R_7$ is lower alkylthio, (lower alkyl)amino, di(lower alkyl)amino, or benzylthio, and when one of $R_5$ and $R_7$ is lower alkylthio, at least another one of $R_2$, $R_5$ and $R_7$ is mercapto, lower alkylthio or lower alkoxy; and pharmaceutically acceptable acid-addition salts of the compounds of Formula I.

"Lower alkyl" as used in the instant specification and claims designates straight and branched-chain alkyl groups containing one to about 4 carbon atoms. Preferred lower alkyl groups are methyl and ethyl.

"Halogen" as used in the instant specification and claims designates fluoro, chloro and bromo.

One preferred class of compounds of Formula I is that wherein $R_8$ is hydrogen. Another preferred class of compounds of Formula I is that wherein both $R_5$ and $R_7$ are lower alkylthio. Still another preferred class of compounds of Formula I is that wherein $R_5$ is N,N-dilower alkylamino and more preferably N-lower alkylamino. Yet another preferred class of compounds of Formula I is that wherein $R_5$ is benzylthio. Still another preferred class of compounds of Formula I is that wherein $R_2$ is alkoxy and $R_5$ or $R_7$ is lower alkylthio. These compounds are preferred because of their generally higher potency in protection against histamine-induced contraction of isolated guinea pig tracheal tissue. This in vitro activity is discussed in greater detail below.

Specific examples of preferred compounds of Formula I which are active in the aforementioned assay at concentrations of 5 µg per ml or lower are:

5-(N,N-diethyl)amino-7-methyl-1,2,4-triazolo[1,5-c]pyrimidine;
2,5-di(methylthio)-7-methyl-1,2,4-triazolo[1,5-c]pyrimidine;
7-methyl-5-(N-methyl)amino-1,2,4-triazolo[1,5-c]pyrimidine;
2-methoxy-7-methyl-5-methylthio-1,2,4-triazolo[1,5-c]pyrimidine;
2-ethyl-5-(N-methyl)amino-1,2,4-triazolo[1,5-c]pyrimidine; and
7-methyl-5-benzylthio-1,2,4-triazolo[1,5-c]pyrimidine.

Some of the above compounds are also active orally in antagonism of histamine-induced bronchial constriction in guinea pigs at doses of 100 mg/kg or less.

The bronchodilator activity of the compounds of Formula I was assessed by the measurement of effects on isolated tracheal spirals. This is a well-known and long established in vitro test method. The bronchodilator activity was determined as follows: Female guinea pigs were sacrificed, and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in µg/ml) required to provide greater than 75% relaxation of drug-induced contraction is considered an effective concentration. For comparison, a well-known standard bronchodilator, aminophylline, requires concentrations of 50 µg/ml versus histamine, 100 µg/ml versus acetylcholine and 10 µg/ml versus barium chloride to provide greater than 75% relaxation.

The compounds of Formula I which were most active in the in vitro test, including some of those listed above as preferred compounds, were tested for oral activity in an in vivo test, that being the so-called histamine aerosol method as described in U.S. Pat. No. 3,248,292. This test was modified slightly in that a 0.1% aqueous solution of histamine was used as the agent for inducing bronchial constriction. Oral doses were measured in mg/kg of body weight of the guinea pig.

Some of the compounds of Formula I were also found to have activity as mucolytics in an in vitro test for mucus production in which rats are orally dosed with compound prior to sacrifice, and the trachea is isolated and incubated with radiolabelled glucosamine. The effect of compounds of Formula I on the incorporation of glucosamine into extracellular mucus is determined. An active compound reduces incorporation of glucosamine.

The compounds of Formula I may be administered to mammals in order to obtain bronchodilation. The compounds may be administered orally, parenterally or by inhalation. Preferably, the compounds are administered orally in the form of tablets or capsules. The usual effective human dose will be 0.1 to 50 mg/kg of body weight.

Acid-addition salts of compounds of Formula I are generally prepared by reaction of a compound of Formula I with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble, an example of such a solvent being diethyl ether.

The compounds of Formula I may be prepared by several synthetic routes.

Reaction Scheme I illustrated below may be used to prepare compounds wherein $R_2$ is hydrogen or lower alkyl; $R_5$ and $R_7$ are independently lower alkylthio; $R_8$ is hydrogen, lower alkyl or halogen; and each "Alk" is independently lower alkyl.

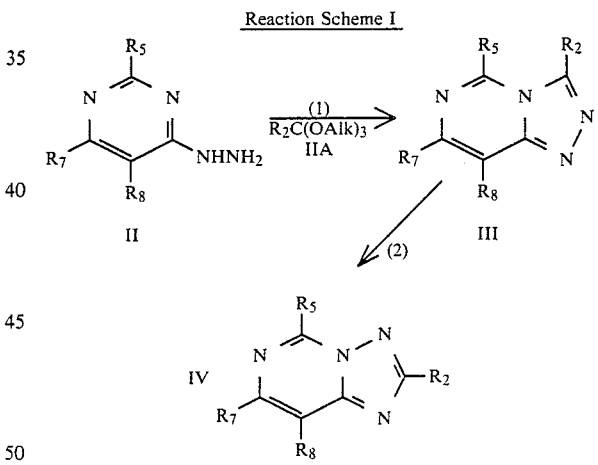

Reaction Scheme I

In step (1) of Reaction Scheme I, a pyrimidylhydrazine of Formula II is reacted with an orthoester of Formula IIA to provide a 1,2,4-triazolo[4,3-c]pyrimidine of Formula III. Orthoesters of Formula IIA are well known and readily available. Examples of suitable orthoesters include trimethyl orthoformate, triethyl orthoformate, triethyl orthoacetate, triethyl orthopropionate and the like. Since the orthoesters of Formula IIA are liquids, it is convenient to mix the pyrimidylhydrazine of Formula II with an excess of orthoester and to heat the mixture at reflux until reaction is complete.

In step (2), the 1,2,4-triazolo[4,3-c]pyrimidine of Formula III is heated with an aqueous acid to provide a 1,2,4-triazolo[1,5-c]pyrimidine of Formula IV. The preferred aqueous acids are carboxylic acids such as formic acid, acetic acid and propionic acid. The reaction mixture is generally heated at reflux for up to several days.

The desired product is isolated by conventional methods. The products are generally white crystalline solids.

Reaction Scheme II illustrated below may be used to prepare compounds wherein $R_2$ is hydroxy or lower alkoxy; $R_5$ is lower alkylthio; $R_7$ is hydrogen, lower alkyl, lower alkylthio or halogen; and $R_8$ is hydrogen, lower alkyl or halogen. Each "Alk" in Reaction Scheme II is independently lower alkyl.

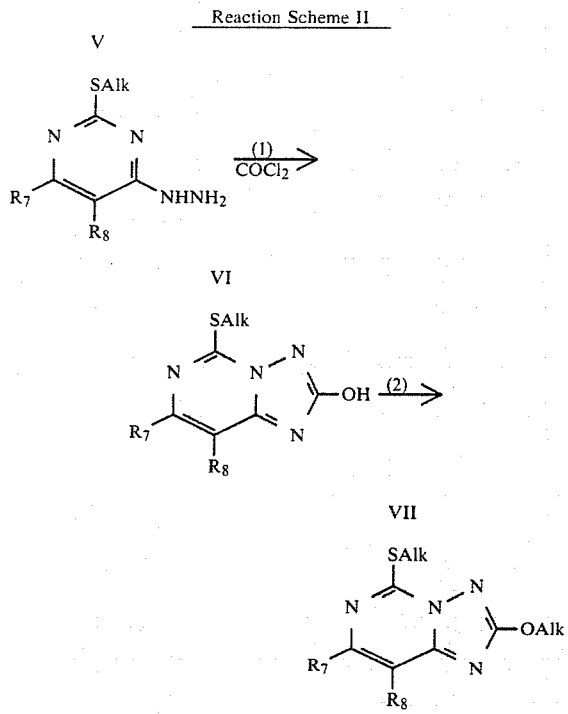

The reaction of step (1) of Reaction Scheme II comprises reacting phosgene with a pyrimidylhydrazine of Formula V to provide the novel compound of Formula VI. Compounds of Formula V are generally known or may be prepared by known methods. Compounds wherein $R_7$ is lower alkylthio may be prepared from known 2-alkylthio-6-chloro-4-hydrazinopyrimidines by reacting the latter with an alkali metal alkylthioate in a suitable solvent such as an alcohol. Suitable alkali metal alkylthioates include sodium methyl mercaptide, potassium methyl mercaptide, sodium ethyl mercaptide and the like. The reaction is generally promoted by heating the mixture to, for example, its reflux temperature. These bis(alkylthio)pyrimidylhydrazines are novel. Compounds wherein both $R_7$ and $R_8$ are halogen are not known and are not used in Reaction Scheme II.

In carrying out step (1), the intermediates of Formula V are combined with phosgene in an inert solvent such as benzene, water, dioxane or the like. The reaction occurs readily without heating. However, the reaction may be promoted with slight heating. The reaction is preferably carried out in the presence of an acid, for example, 2N hydrochloric acid or acetic acid. The solid product of Formula III is readily isolated by conventional techniques.

In step (2) of Reaction Scheme II, the compound of Formula VI is alkylated on the 2-hydroxy group to provide 2-alkoxy derivatives. Such alkylation occurs readily by reaction of a compound of Formula VI with a lower alkyl halide, generally a lower alkyl bromide or iodide. The reaction is carried out in an inert solvent, preferably an alcohol such as methanol, in the presence of a strong base, for example, sodium methoxide or sodium ethoxide. The reaction is generally heated to, for example, the reflux temperature of the reaction mixture to speed the rate of reaction. The compounds of Formula VII are solids which are readily isolated by conventional methods.

Reaction Scheme III illustrated below may be used to prepare compounds of Formula I wherein $R_2$ is mercapto or lower alkylthio; $R_5$ is lower alkylthio; $R_7$ is hydrogen, lower alkyl, lower alkylthio or halogen; and $R_8$ is hydrogen or lower alkyl. Each "Alk" is Reaction Scheme III is independently lower alkyl.

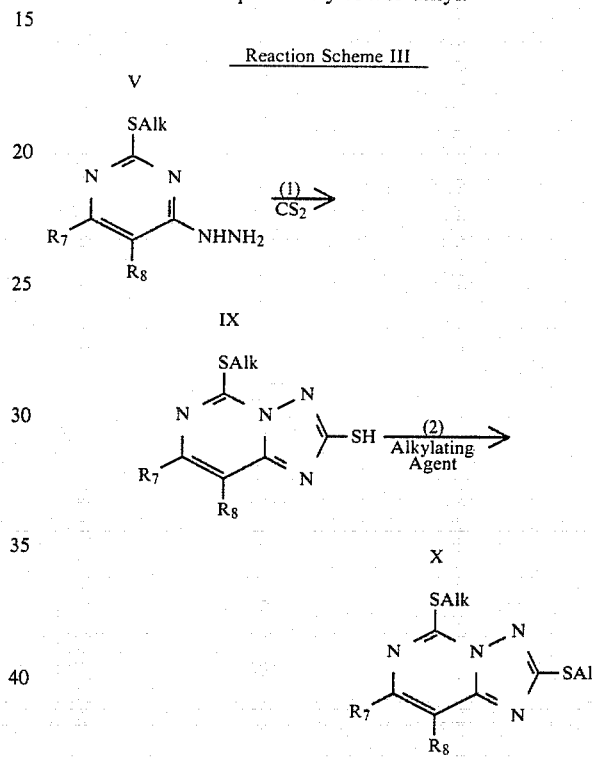

In step (1) of Reaction Scheme III, the compound of Formula V is reacted with carbon disulfide in an inert solvent such as n-butanol or pyridine. The reaction mixture is generally heated at reflux. The product of Formula IX is generally a solid which may be readily isolated by conventional methods.

The process of step (2) is the alkylation of the 2-thio group of the compounds of Formula IX. It is carried out by reacting the compound of Formula IX with an alkylating agent such as, for example, dimethyl sulfate or an alkyl halide, in the presence of base and in an inert solvent such as water (in the case of dimethyl sulfate) or a lower alkanol. The base is generally sodium carbonate, sodium hydride, or an alkali metal alkoxide. The product of Formula X is generally a solid which may be readily isolated by conventional methods.

Reaction Scheme IV illustrated below may be used to prepare compounds wherein $R_2$ is hydrogen, lower alkyl, mercapto, lower alkylthio, lower alkoxy or hydroxy; $R_5$ is benzylthio; $R_7$ is hydrogen, lower alkyl, halogen, or lower alkylthio; $R_8$ is hydrogen, lower alkyl or halogen, and is hydrogen or lower alkyl when $R_7$ is halogen; and X is halogen.

Reaction Scheme IV

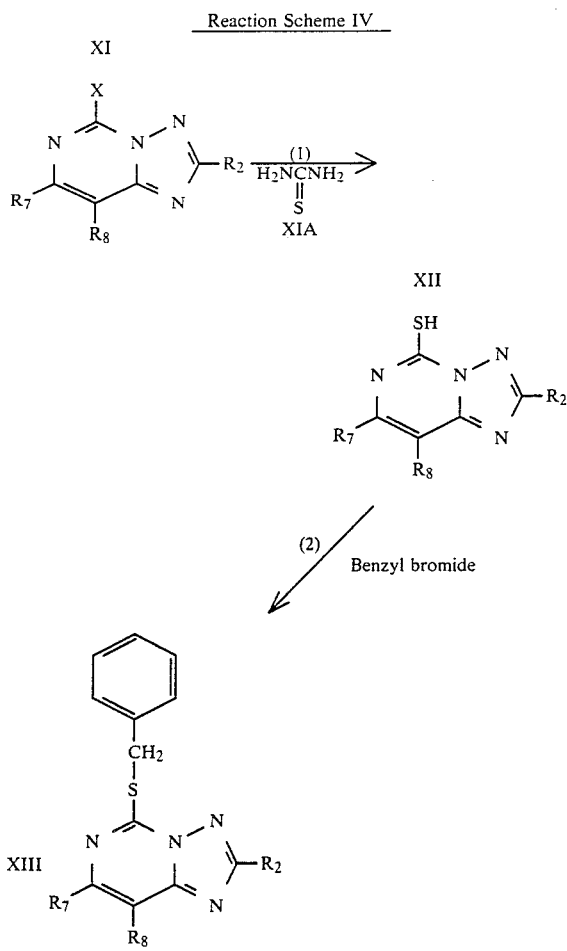

In step (1) of Reaction Scheme IV, a triazolo[1,5-c]pyrimidine of Formula XI is reacted with thiourea (Formula XIA) to provide the intermediate of Formula XII. The reactants are combined in a suitable non-reactive solvent such as a lower alkanol, and the reaction mixture is generally heated at, for example, its reflux temperature. The products are solids which are readily isolated by conventional methods.

The triazolo[1,5-c]pyrimidine of Formula XII is reacted with benzyl bromide in step (2). The reactants are heated with an aqueous base such as an alkali metal hydroxide to provide the product of Formula XIII which is generally a solid that may be isolated by conventional methods.

Compounds of Formula I wherein $R_5$ is (lower alkyl)amino or di(lower alkyl)amino are prepared from the corresponding compounds wherein $R_5$ is halogen by reaction of the latter with a (lower alkyl)amine or di(-lower alkyl)amine in water or other suitable solvent such as diethyl ether, dioxane, a lower alkanol or the like. Heating, for example, at the reflux temperature, may be employed to accelerate the rate of reaction. The product is generally a solid which may be readily isolated by conventional methods.

Compounds of Formula I wherein $R_7$ is (lower alkyl)amino or di(lower alkyl)amino are prepared by cyclizing the hydrazinopyrimidines which are substituted in the 6 position by a (lower alkyl)amino or di(lower alkyl)amino group. Such substituted hydrazinopyrimidines are generally known compounds or may be prepared by conventional methods.

Compounds of Formula I wherein $R_5$ or $R_7$ is lower alkyl are prepared by cyclizing the 4-hydrazinopyrimidines which are substituted in the 2- and/or 6-position by a lower alkyl group. Such substituted 4-hydrazinopyrimidines are generally known or may be prepared by conventional methods.

The assignment of the ring structure of the compounds of the invention is internally consistent, i.e. all compounds of the invention are prepared by cyclization reactions such as those of Scheme I which would be expected to provide the same heterocyclic ring. The 1,5-c configuration is assigned by analogy to the work of Miller and Rose, *J. Chem. Soc.* 1963, 5642; 1965, 3357; and 1965 3369.

The following examples are provided to illustrate the methods used in the invention. They are not intended to limit the invention.

EXAMPLE 1

Preparation of a 2,6-Bis(alkylthio)-4-hydrazinylpyrimidine

A mixture of the known compound 6-chloro-4-hydrazinyl-2-methylthiopyrimidine (15 g, 0.079 mole) and 21 g (0.1 mole) of sodium methyl mercaptide in 250 ml of methanol was heated at reflux for about 16 hours, and was then allowed to cool to about 20° C. The solid precipitate was separated by filtration, washed with methanol and water and dried. The filtrate was evaporated to provide a solid residue. This residue was then washed thoroughly with water and combined with the precipitate. The solids were dissolved in 500 ml of acetic acid, and the solution was treated with decolorizing charcoal, and filtered. The filtrate was cooled and treated with ammonium hydroxide until it was slightly basic. The precipitate was collected by filtration, providing 10.5 g (65%) of 2,6-bis(methylthio)-6-hydrazinylpyrimidine, m.p. 120°–125° C.

EXAMPLES 2–5

Using the method of Example 1 and starting with the indicated intermediates, the following novel intermediate compounds of Formula II of the invention may be prepared (Table I).

TABLE I

| Ex. No. | Pyrimidine Starting Material | Metal Mercaptide Starting Material | Product of Formula II |
|---|---|---|---|
| 2 | 6-chloro-4-hydrazinyl-2-methylthiopyrimidine | potassium n-butyl mercaptide | 4-(n-butyl)thio-6-hydrazinyl-2-methylthiopyrimidine |
| 3 | 6-chloro-4-hydrazinyl-2-methylthiopyrimidine | sodium isopropyl mercaptide | 6-hydrazinyl-4-isopropylthio-2-methylthiopyrimidine |
| 4 | 2-(n-butyl)thio-6-chloro-4-hydrazinylpyrimidine | sodium methyl mercaptide | 2-(n-butyl)thio-6-hydrazinyl-4-methylthiopyrimidine |
| 5 | 6-chloro-4-hydrazinyl-2-isopropylthiopyrimidine | sodium ethyl mercaptide | 4-ethylthio-6-hydrazinyl-2-isopropylthiopyrimidine |

EXAMPLE 6

Preparation of
5,7-Bis(methylthio)-2-hydroxytriazolo[1,5-c]pyrimidine

Into a solution of 2.5 g (12 mmole) of 2,6-bis-(methylthio)-4-hydrazinopyrimidine (from Example 1) in 25 ml of 2N hydrochloric acid was bubbled gaseous phosgene. A precipitate formed, and addition of phosgene was continued until no more precipitate formed. Filtration and recrystallization from glyme with treatment with decolorizing charcoal provided 5,7-bis(methylthio)-2-hydroxytriazolo[1,5-c]pyrimidine, m.p. 275°–278° C. Analysis: Calculated for $C_7H_8N_4OS_2$: %C, 36.8; %H, 3.5; %N, 24.5; Found: % C, 36.6; %H, 3.4; %N, 24.6.

EXAMPLE 7

Preparation of
7-Chloro-2-hydroxy-5-methylthiotriazolo[1,5-c]pyrimidine

To a stirred solution of 0.04 mole of phosgene at a concentration of 12.5% in benzene was added a warm solution of 3.8 g (0.02 mole) of 4-chloro-2-methylthio-6-hydrazinylpyrimidine which had been dissolved by warming in 30 ml of dioxane. After one hour the solid product was collected by filtration and washed with hexane and water. Recrystallization from a 50:50 glyme/hexane mixture provided yellow crystals of 7-chloro-2-hydroxy-5-methylthiotriazolo[1,5-c]pyrimidine, m.p. 256°–257° C. Analysis: Calculated for $C_6H_5ClN_4OS$: %C, 33.3; %H, 2.3; %N, 25.9; Found: %C, 33.4; %H, 2.0; %N, 26.2

EXAMPLE 8

Preparation of
2-Hydroxy-7-methyl-5-methylthiotriazolo[1,5-c]pyrimidine

Into a stirred solution of 2.0 g (12 mmole) of 4-hydrazino-6-methyl-2-methylthiopyrimidine in 50 ml of 20% aqueous acetic acid and 7.0 g (85 mmole) of sodium acetate was bubbled phosgene gas for 10 minutes. The precipitate which formed was collected by filtration and recrystallized from a 50:50 mixture of glyme and hexane with treatment with decolorizing charcoal. The product was white crystals of 2-hydroxy-7-methyl-5-methylthiotriazolo[1,5-c]pyrimidine. Analysis: Calculated for $C_7H_8N_4OS$: %C, 42.8; %H, 4.1; %N, 28.6; Found: %C, 42.7; %H, 4.0; %N, 28.6.

EXAMPLES 9–15

Using the methods of Examples 6, 7 and 8, the indicated intermediates of Formula II may be reacted with phosgene to prepare the indicated compounds of Formula III (Table II).

TABLE II

| Ex. No. | Starting Material of Formula II | Product of Formula III |
|---|---|---|
| 9 | 5-bromo-4-hydrazinyl-2-methylthiopyrimidine | 8-bromo-5-methylthio-2-hydroxytriazolo[1,5-c]pyrimidine |
| 10 | 4-(n-butyl)thio-6-hydrazinyl-2-methylthiopyrimidine | 7-(n-butyl)thio-2-hydroxy-5-methylthiotriazolo[1,5-c]pyrimidine |
| 11 | 4-ethylthio-6-hydrazinyl-2-isopropylthiopyrimidine | 7-ethylthio-2-hydroxy-5-isopropylthiotriazolo[1,5-c]pyrimidine |
| 12 | 4-chloro-2-ethylthio-6-hydrazinylpyrimidine | 5-ethylthio-2-hydroxy-7-chlorotriazolo[1,5-c]pyrimidine |
| 13 | 4-chloro-6-hydrazinyl-2-(n-butylthio)pyrimidine | 5-(n-butylthio)-7-chloro-2-hydroxytriazolo[1,5-c]pyrimidine |
| 14 | 2,6-bis(ethylthio)-6-hydrazinylpyrimidine | 5,7-bis(ethylthio)-2-hydroxytriazolo[1,5-c]pyrimidine |
| 15 | 4-ethyl-2-methylthio-6-hydrazinylpyrimidine | 7-ethyl-2-hydroxy-5-methylthiotriazolo[1,5-c]pyrimidine |

EXAMPLE 16

Alkylation of a Compound of Formula III

A mixture of 2.0 g (0.01 mole) of 2-hydroxy-7-methyl-5-methylthiotriazolo[1,5-c]pyrimidine (from Example 8), 1.5 g (0.01 mole) of methyl iodide, 5 g (0.023 mole) of sodium methoxide (as a 25% methanolic solution), and 40 ml of methanol was heated at its reflux temperature for two hours. The mixture was cooled to about 0° C., and the precipitate was collected by filtration. After washing the precipitate with water, the product was recrystallized from a 50:50 ethanol-hexane mixture with treatment with decolorizing charcoal. The product was white needles of 2-methoxy-7-methyl-5-methylthiotriazolo[1,5-c]pyrimidine, m.p. 202°–204° C. Analysis: Calculated for $C_8H_{10}N_4OS$: %C, 45.7; %H, 4.8; %N, 26.6; Found: %C, 45.6; %H, 4.7; %N, 26.6.

EXAMPLE 17

Preparation of
7-Chloro-2-methoxy-5-methylthiotriazolo[1,5-c]pyrimidine

A mixture of 1.2 g (5 mmole) of 7-chloro-2-hydroxy-5-methylthiotriazolo[1,5-c]pyrimidine (from Example 7), 2 g (14 mmole) of methyl iodide, 1.2 g (5 mmole) of sodium methoxide (as a 25% methanolic solution), and 50 ml of methanol was heated at its reflux temperature for two hours and then cooled. The solid was collected by filtration and recrystallized from a 50:50 mixture of glyme and hexane to provide yellow crystals of 7-chloro-2-methoxy-5-methylthiotriazolo[1,5-c]pyrimidine, m.p. 243°–244° C. Analysis: Calculated for $C_7H_7ClN_4OS$: %C, 36.4; %H, 3.1; %N, 24.3; Found: %C, 36.3; %H, 2.9; %N, 24.2.

EXAMPLES 18–22

Using the method of Examples 16 and 17, the indicated compounds of Formula III may be reacted with the indicated alkyl halides to provide the compounds of Formula I (Table IV).

TABLE III

| Ex. No. | Compound of Formula III | Alkyl Halide | Product of Formula I |
|---|---|---|---|
| 18 | 8-bromo-5-methylthio-2-hydroxytriazolo[1,5-c]pyrimidine | n-butyl bromide | 8-bromo-2-(n-butoxy)-5-methylthiotriazolo[1,5-c]pyrimidine |
| 19 | 8-bromo-5-methylthio-2-hydroxytriazolo[1,5-c]pyrimidine | methyl iodide | 8-bromo-2-methoxy-5-methylthiotriazolo[1,5-c]pyrimidine |
| 20 | 5,7-bis(methylthio)-2-hydroxytriazolo[1,5-c]pyrimidine | methyl iodide | 5,7-bis(methylthio)-2-methoxytriazolo[1,5-c]pyrimidine |
| 21 | 5,7-bis(methylthio)-2-hydroxytriazolo[1,5-c]pyrimidine | ethyl iodide | 5,7-bis(methylthio)-2-ethoxytriazolo[1,5-c]pyrimidine |
| 22 | 7-(n-butyl)thio-2-hydroxy-5-methylthiotriazolo-[1,5-c]pyrimidine | methyl iodide | 7-(n-butyl)thio-2-methoxy-5-methylthiotriazolo-[1,5-c]pyrimidine |

EXAMPLE 23

Preparation of a 5-Alkylthiotriazolo[1,5-c]pyrimidine-2-thiol

A mixture of 4.0 g (20 mmole) of 2,6-bis(methylthio)-4-hydrazinylpyrimidine and 3.0 g (40 mmole) of carbon disulfide in 20 ml of n-butanol was heated at its reflux temperature for eight hours, and was then cooled to 0° C. The product was collected by filtration and recrystallized from aqueous N,N-dimethylformamide with treatment with decolorizing charcoal to provide tan crystals of 5,7-bis(methylthio)triazolo[1,5-c]pyrimidine-2-thiol, m.p. 250°–252° C. Analysis: Calculated for $C_7H_8N_4S_3$: %C, 34.4; %H, 3.3; %N, 22.9; Found: %C, 34.8; %H, 3.2; %N, 23.4.

EXAMPLE 24

Preparation of 8-Bromo-5-methylthiotriazolo[1,5-c]pyrimidine-2-thiol

Using the method of Example 23, but starting with 5-bromo-4-hydrazinyl-2-methylthiopyrimidine (instead of 2,6-bis(methylthio)-4-hydrazinylpyrimidine) and using pyridine in place of n-butanol, a yellow solid 8-bromo-5-methylthiotriazolo[1,5-c]pyrimidine-2-thiol, m.p. 244°–245° C., was obtained. Analysis: Calculated for $C_6H_5BrN_4S$: %C, 26.0; %H, 1.8; %N, 20.2; Found: %C, 25.9; %H, 1.7; %N, 20.3.

EXAMPLE 25

Preparation of 7-Methyl-5-methylthiotriazolo[1,5-c]pyrimidine-2-thiol

Using the method of Example 23, but starting with 4-hydrazinyl-6-methyl-2-methylthiopyrimidine (instead of 2,6-bis(methylthio)-4-hydrazinylpyrimidine), yellow crystals of 7-methyl-5-methylthiotriazolo[1,5-c]pyrimidine-2-thiol, m.p. 256°–258° C., were obtained.

EXAMPLES 26–27

Using the method of Example 23, the indicated intermediates of Formula II described in the following Table IV may be used to prepare the indicated compounds of Formula V.

TABLE IV

| Ex. No. | Starting Material of Formula II | Product of Formula V |
|---|---|---|
| 26 | 4-(n-butyl)thio-6-hydrazinyl-2-methylthiopyrimidine | 7-(n-butyl)thio-5-methylthio-triazolo[1,5-c]pyrimidine-2-thiol |
| 27 | 4-ethylthio-6-hydrazinyl-2-isopropylthiopyrimidine | 7-ethylthio-5-isopropylthio-triazolo[1,5-c]pyrimidine-2-thiol |

EXAMPLE 28

Preparation of a 2,5-Bis(alkylthio)triazolo[1,5-c]pyrimidine

A mixture of 1.4 g (0.007 mole) of 7-methyl-5-methylthiotriazolo[1,5-c]pyrimidine-2-thiol (from Example 25) and 1.5 g of sodium carbonate in 50 ml of water was heated to 60° C. to obtain a solution. To this stirred solution was added 1.33 g (0.01 mole) of dimethyl sulfate. After cooling to about 20° C., the solid was collected by filtration, washed with water and recrystallized from an ethanol-heptane mixture with treatment with decolorizing charcoal. The product was yellow crystals of 2,5-bis(methylthio)-7-methyltriazolo[1,5-c]pyrimidine, m.p. 167°–171° C. Analysis: Calculated for $C_8H_{10}N_4S_2$: %C, 42.5; %H, 4.5; %N, 24.8; Found: %C, 42.9; %H, 4.4; %N, 24.8.

EXAMPLE 29

Alternative Preparation of a 2,5-Bis(alkylthio)triazolo[1,5-c]pyrimidine

A solution of 2.5 g (9 mmole) of 8-bromo-5-methylthiotriazolo[1,5-c]pyrimidine-2-thiol (from Example 24), 2.2 g of sodium methoxide (as a 25% solution in methanol) and 1.5 g of methyl iodide in 40 ml of methanol was heated at reflux for four hours, and was then cooled and evaporated to dryness. Water was added to the residue and the solid obtained was recrystallized from an ethanol-hexane mixture with treatment with decolorizing charcoal. The product was white solid 2,5-bis(methylthio)-8-bromotriazolo[1,5-c]pyrimidine, m.p. 168°–171° C. Analysis: Calculated for $C_7H_7BrN_4S_2$: %C, 28.9; %H, 2.4; %N, 19.2; Found: %C, 28.8; %H, 2.3; %N, 19.7.

EXAMPLE 30

Preparation of 2,5,7-Tris(methylthio)triazolo[1,5-c]pyrimidine

Using the method of Example 28 and starting with 5,7-bis(methylthio)triazolo[1,5-c]pyrimidine-2-thiol (from Example 23) and dimethyl sulfate, a solid was obtained which was recrystallized from an ethyl acetate-hexane mixture to provide 2,5,7-tris(methylthio)- triazolo[1,5-c]pyrimidine, m.p. 165°–167° C. Analysis: Calculated for $C_8H_{10}N_4S_3$: %C, 37.2; %H, 3.9; %N, 21.7; Found: %C, 37.5; %H, 3.9; %N, 22.0.

EXAMPLES 31–32

Using the methods of Examples 28 and 29, the indicated compounds of Formula V may be alkylated with the indicated alkylating agent to provide the indicated products shown (Table V).

TABLE V

| Ex. No. | Starting Material of Formula IV | Alkylating Agent | Product of Formula I |
|---|---|---|---|
| 31 | 7-(n-butylthio)-5-methylthio-triazolo[1,5-c]-pyrimidine-2-thiol | $(CH_3)_2SO_4$ | 2,5-bis(methylthio)-7-(n-butylthio)triazolo[1,5-c]-pyrimidine |
| 32 | 7-ethylthio-5-isopropylthio-triazolo[1,5-c]-pyrimidine-2-thiol | $(CH_3)_2SO_4$ | 7-ethylthio-5-isopropyl-thio-2-methylthiotriazolo-[1,5-c]pyrimidine |

Some intermediate compounds wherein $R_5$ is chloro and $R_2$ and/or $R_7$ are alkyl are known, and those which are not known can be prepared by the methods known to the art, e.g., that disclosed in Aust. J. Chem. 1979, 32, 1585–93, incorporated herein by reference. Such intermediates are used in Examples 33 to 36 inclusive.

EXAMPLE 33

Preparation of 7-Methyltriazolo[1,5-c]pyrimidine-5-thiol

A mixture of 14.5 g (85 mmole) of 5-chloro-7-methyltriazolo[1,5-c]pyrimidine and 15 g (200 mmole) of thiourea in 100 ml of methanol was heated at reflux for one hour, and then cooled to 0° C. The product was collected by filtration and recrystallized from a 50:50 mixture of ethanol and hexanes with treatment with decolorizing charcoal to provide 7-methyltriazolo[1,5-c]pyrimidine-5-thiol. The structural assignment was confirmed by nuclear magnetic resonance spectral analysis.

EXAMPLE 34

Preparation of 2-Methyltriazolo[1,5-c]pyrimidine-5-thiol

Using the method of Example 33, 5-chloro-2-methyltriazolo[1,5-c]pyrimidine was converted to white crystals of 2-methyltriazolo[1,5-c]pyrimidine-5-thiol, m.p. >300° C. Analysis: Calculated for $C_6H_6N_4S$: %C, 43.4; %H, 3.6; %N, 33.7; Found: %C, 43.4; %H, 3.4; %N, 33.7.

EXAMPLE 35

Preparation of 2-Ethyltriazolo[1,5-c]pyrimidine-5-thiol

Using the method of Example 33, 5-chloro-2-ethyltriazolo[1,5-c]pyrimidine was converted to white crystals of 2-ethyltriazolo[1,5-c]pyrimidine-5-thiol, m.p. 251°–254° C. Analysis: Calculated for $C_7H_8N_4S$: %C, 46.6; %H, 4.5; %N, 31.3; Found: %C, 46.6; %H, 4.2; %N, 31.2.

EXAMPLE 36

Preparation of 2,7-Dimethyltriazolo[1,5-c]pyrimidine-5-thiol

Using the method of Example 33, 5-chloro-2,7-dimethyltriazolo[1,5-c]pyrimidine was converted to 2,7-dimethyltriazolo[1,5-c]pyrimidine-5-thiol.

EXAMPLES 37–39

Using the method of Example 33, the indicated halogen-substituted triazolo[1,5-c]pyrimidines may be converted to the indicated triazolo[1,5-c]pyrimidinethiols (Table VI).

TABLE VI

| Ex. No. | Starting Material | Product |
|---|---|---|
| 37 | 5-chloro-2-methyl-7-methylthio-triazolo[1,5-c]pyrimidine | 2-methyl-7-methylthio-triazolo[1,5-c]pyrimidine-5-thiol |
| 38 | 7-(n-butylthio)-5-chloro-2-methyltriazolo[1,5-c]pyrimidine | 7-(n-butylthio)-2-methyl-triazolo[1,5-c]pyrimidine-5-thiol |
| 39 | 5-chloro-2-(n-propyl)triazolo-[1,5-c]pyrimidine | 2-(n-propyl)triazolo-[1,5-c]pyrimidine-5-thiol |

EXAMPLE 40

Preparation of a Benzylthio-substituted Triazolo[1,5-c]pyrimidine

A mixture of 2.5 g (15 mmole) of 7-methyltriazolo[1,5-c]pyrimidine-5-thiol (from Example 33), 4 g (24 mmole) of benzyl bromide and 0.8 g (20 mmole) of sodium hydroxide in 50 ml of water was heated at its reflux temperature for 2.5 hours, and was then allowed to cool to about 20° C. The solution was extracted thrice with 100 ml of chloroform, and the extracts were dried and then evaporated to provide an oil which solidified after scratching. Recrystallization of the solid from hexane with treatment with decolorizing charcoal provided white solid 5-benzylthio-7-methyltriazolo[1,5-c]pyrimidine, m.p. 74°–75° C. Analysis: Calculated for $C_{13}H_{12}N_4S$: %C, 60.9; %H, 4.7; %N, 21.9; Found: %C, 61.3; %H, 4.7; %N, 21.8.

EXAMPLE 41

Preparation of 5-Benzylthio-2,7-dimethyltriazolo[1,5-c]pyrimidine

Using the method of Example 40, 2,7-dimethyltriazolo[1,5-c]pyrimidine-5-thiol (from Example 36) was converted to 5-benzylthio-2,7-dimethyltriazolo[1,5-c]pyrimidine, m.p. 108°–111° C., after recrystallization from cyclohexane with treatment with decolorizing charcoal. Analysis: Calculated for $C_{14}H_{14}N_4S$: %C, 62.2; %H, 5.2; %N, 20.7; Found: %C, 62.4; %H, 5.2; %N, 20.8.

EXAMPLES 42–46

Using the method of Example 41, the indicated triazolo[1,5-c]pyrimidinethiols may be converted to the indicated benzylthio-substituted triazolo[1,5-c]pyrimidines (Table VII).

TABLE VII

| Ex. No. | Starting Material | Product |
|---|---|---|
| 42 | 2-methyltriazolo-[1,5-c]pyrimidine-5-thiol | 5-benzylthio-2-methyltriazolo-[1,5-c[pyrimidine |
| 43 | 2-ethyltriazolo[1,5-c]-pyrimidine-5-thiol | 5-benzylthio-2-ethyltriazolo-[1,5-c]pyrimidine |
| 44 | 2-(n-propyl)triazolo-[1,5-c]pyrimidine-5-thiol | 5-benzylthio-2-(n-propyl)triazolo-[1,5-c]pyrimidine |
| 45 | 2-methyl-7-methylthio-triazolo[1,5-c]pyrimi-dine-5-thiol | 5-benzylthio-2-methyl-7-methyl-thiotriazolo[1,5-c]pyrimidine |
| 46 | 7-(n-butylthio)-2-methyl-triazolo[1,5-c]pyrimi-dine-5-thiol | 5-benzylthio-7-(n-butylthio)-2-methyltriazolo[1,5-c]pyrimidine |

EXAMPLE 47

Preparation of
5-(N,N-diethylamino)-7-methyltriazolo[1,5-c]pyrimidine

To a stirred solution of 2.5 g (15 mmole) of 5-chloro-2-methyltriazolo[1,5-c]pyrimidine in 50 ml of dioxane was added 2.2 g (30 mmole) of N,N-diethylamine. After stirring for three hours at about 20° C., the solid was separated by filtration and washed with dioxane. The filtrate and washings were evaporated to provide a residue which was dissolved in 150 ml of chloroform. The solution was washed thrice with 50 ml portions of water and once with 50 ml of saturated sodium chloride solution, and was then dried over magnesium sulfate. Evaporation of the chloroform provided an oil which solidified when cooled with dry ice. The solid was suspended in hexane, and the mixture was cooled to 0° C. Filtration provided a yellow solid which was purified by high pressure liquid chromatography with chloroform as the eluent. The middle fractions provided a residue which was triturated with diethyl ether and dried. The white solid product was 5-(N,N-diethylamino)-7-methyltriazolo[1,5-c]pyrimidine, m.p. 57°–58° C. Analysis: Calculated for $C_{10}H_{15}N_5$: %C, 58.5; %H, 7.4; %N, 34.1; Found: %C, 58.4; %H, 7.5; %N, 34.0.

EXAMPLE 48

Preparation of
7-Methyl-5-(N-methylamino)triazolo[1,5-c]pyrimidine

To a stirred solution of 3.4 g (20 mmole) of 5-chloro-7-methyltriazolo[1,5-c]pyrimidine in 50 ml of water was added 1.25 g (40 mmole) of methylamine as a 40% aqueous solution. The mixture was heated in an oil bath and thickened rapidly as a result. The solid was separated by filtration, and was then recrystallized from a benzene-hexane mixture with treatment with decolorizing charcoal. The product was white needles of 7-methyl-5-(N-methylamino)triazolo[1,5-c]pyrimidine, m.p. 162°–164° C. Analysis: Calculated for $C_7H_9N_5$: %C, 51.5; %H, 5.6; %N, 42.9; Found: %C, 51.6; %H, 5.4; %N, 43.1.

EXAMPLES 49–52

Using the method of Example 48, the indicated halogen-substituted starting materials were reacted with methylamine to provide the indicated products (Table VIII).

TABLE VIII

| Ex. No. | Starting Material | Product | Calculated: % C; % H; % N Found: % C; % H; % N (m.p. in °C.) |
|---|---|---|---|
| 49 | 5-chloro-2-methyl-triazolo[1,5-c]-pyrimidine | 2-methyl-5-(N—methyl-amino)triazolo[1,5-c]-pyrimidine | 51.5; 5.5; 42.9 51.6; 5.5; 42.9 (139–142) |
| 50 | 5-chloro-2-ethyl-triazolo[1,5-c]-pyrimidine | 2-ethyl-5-(N—methyl-amino)triazolo[1,5-c]-pyrimidine | 54.2 6.2; 39.5 54.2; 6.3; 39.5 (75–77) |
| 51 | 5-chloro-2,7-di-methyltriazolo-[1,5-c]pyrimidine | 2,7-dimethyl-5-(N—methylamino)triazolo-[1,5-c]pyrimidine | 54.2; 6.3; 39.5 54.2; 6.3; 40.1 (165–167) |
| 52 | 5-chloro-2-ethyl-7-methyltriazolo-[1,5-c]pyrimidine | 2-ethyl-7-methyl-5-(N—methylamino)triazolo-[1,5-c]pyrimidine | 56.5; 6.8; 36.6 56.1; 6.8; 37.1 (112–114) |

EXAMPLES 53–55

Using the method of Example 48, the indicated halogen-substituted starting materials may be reacted with the indicated amines to provide the indicated products (Table IX).

TABLE IX

| Ex. No. | Triazolo[1,5-c]Pyrimidine Starting Material | Amine Starting Material | Product |
|---|---|---|---|
| 53 | 5-chloro-2-(n-propyl)-triazolo[1,5-c]pyrimidine | N,N—dimethyl-amine | 5-(N,N—dimethylamino)-2-(n-propyl)triazolo[1,5-c]-pyrimidine |
| 54 | 5-chloro-2-methyl-7-methylthiotriazolo-[1,5-c]pyrimidine | N—(n-butyl)-amine | 5-(N—n-butylamino)-2-methyl-7-methylthio-triazolo[1,5-c]pyrimidine |
| 55 | 5-chloro-2-methyl-triazolo[1,2-c]pyrimidine | N,N—di(n-butyl)amine | 5-(N,N—di-n-butylamino)-2-methyltriazolo[1,5-c]-pyrimidine. |

What is claimed is:

1. A compound of the formula:

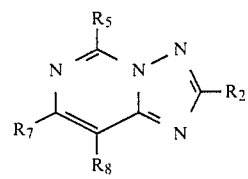

wherein $R_2$ is hydrogen or lower alkyl; $R_5$ is benzylthio; and $R_7$ and $R_8$ are independently hydrogen or lower alkyl; or a pharmaceutically acceptable acid-addition salt thereof.

2. A compound of the formula:

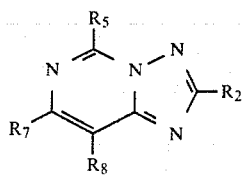

wherein $R_2$ is mercapto, lower alkoxy, lower alkylthio or hydroxy; $R_5$ is lower alkylthio; $R_7$ is hydrogen, lower alkyl, lower alkylthio or halogen; and $R_8$ is hydrogen, lower alkyl, or halogen; or a pharmaceutically acceptable acid-addition salt thereof.

3. A compound of the formula:

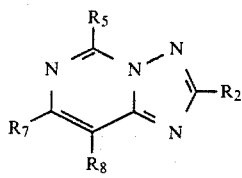

wherein $R_2$ is hydroxy; $R_5$ is lower alkylthio; $R_7$ is hydrogen, lower alkyl, lower alkylthio, or halogen; and $R_8$ is hydrogen or lower alkyl; or a pharmaceutically acceptable acid-addition salt thereof.

4. A bronchodilator pharmaceutical composition comprising an effective amount of a compound according to claim 1 and a pharmaceutically acceptable carrier.

5. A bronchodilator pharmaceutical composition comprising an effective amount of a compound according to claim 2 and a pharmaceutically acceptable carrier.

6. A bronchodilator pharmaceutical composition comprising an effective amount of a compound according to claim 3 and a pharmaceutically acceptable carrier.

7. A method for obtaining bronchodilation in a mammal, wherein an effective amount of a bronchodilator compound is administered to said mammal, said bronchodilator compound being of the formula

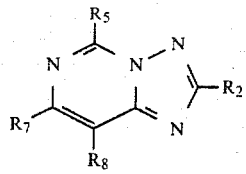

wherein $R_2$ is hydrogen, lower alkyl, mercapto, lower alkylthio, lower alkoxy or hydroxy; $R_5$ is (lower alkyl)amino, di(lower alkyl)amino, alklthio or benzylthio; $R_7$ is hydrogen, lower alkyl, halogen or lower alkylthio; and $R_8$ is hydrogen, lower alkyl or halogen, and is hydrogen or lower alkyl when $R_7$ is halogen; with the provisos that at least one of $R_5$ and $R_7$ is lower alkylthio, (lower alkyl)amino, di(lower alkyl)amino, or benzylthio; and when one of $R_5$ and $R_7$ is lower alkylthio, at least another one of $R_2$, $R_5$ and $R_7$ is mercapto, lower alkylthio or lower alkoxy; or a pharmaceutically acceptable acid-addition salt thereof.

8. A method according to claim 7, wherein said compound is administered orally.

* * * * *